United States Patent [19]

Lord, III

[11] Patent Number: 4,632,563
[45] Date of Patent: Dec. 30, 1986

[54] IN-SITU GAS ANALYZER

[75] Inventor: Harry C. Lord, III, Pasadena, Calif.

[73] Assignee: The Syconex Corporation, San Dimas, Calif.

[21] Appl. No.: 619,818

[22] Filed: Jun. 12, 1984

Related U.S. Application Data

[63] Continuation-in-part of Ser. No. 470,146, Feb. 28, 1983, abandoned.

[51] Int. Cl.$^4$ ............................................. G01N 21/35
[52] U.S. Cl. .................................... 356/437; 250/338; 250/343; 356/51
[58] Field of Search ......................... 356/51, 418, 437; 250/343, 338 GA, 347

[56] References Cited

U.S. PATENT DOCUMENTS

| | | | |
|---|---|---|---|
| 3,287,556 | 11/1966 | Good | 250/338 GA |
| 3,811,776 | 5/1974 | Blau, Jr. | 356/51 |
| 3,853,407 | 12/1974 | Dewey, Jr. | 356/51 |
| 3,869,613 | 3/1975 | Link et al. | 250/343 |
| 3,904,880 | 9/1975 | Benz et al. | 250/343 |
| 3,976,884 | 8/1976 | Action et al. | 250/343 |
| 4,126,396 | 11/1978 | Hartmann et al. | 356/418 |
| 4,205,550 | 6/1980 | Swanson | 356/438 X |

FOREIGN PATENT DOCUMENTS 1136882 12/1982 Canada ................................. 356/319

Primary Examiner—F. L. Evans
Attorney, Agent, or Firm—Donald D. Mon

[57] ABSTRACT

A gas analyzer which utilizes an infrared beam which passes through or has emanated from a gas stream. The analyzer has a plurality of gas cells which contain gas of the type whose concentration is being measured in various concentrations and at various total pressures. A beam of energy is forwarded to the analyzer, and is passed selectively to the various cells. In one embodiment, the cells are mounted where a rotatable deflector can selectively deflect and receive the beam to and from two fixed beam segments so that sequential readings at an infrared detector can provide measurements of concentrations, and calibration. In another embodiment, the cells are selectively moved into the beam path. The beam is formed and forwarded by a Cassegrainean system or by a combination of reflectors including a retro-reflector. An infrared calibration beam which does not pass through the gas stream is utilized for calibration.

23 Claims, 12 Drawing Figures

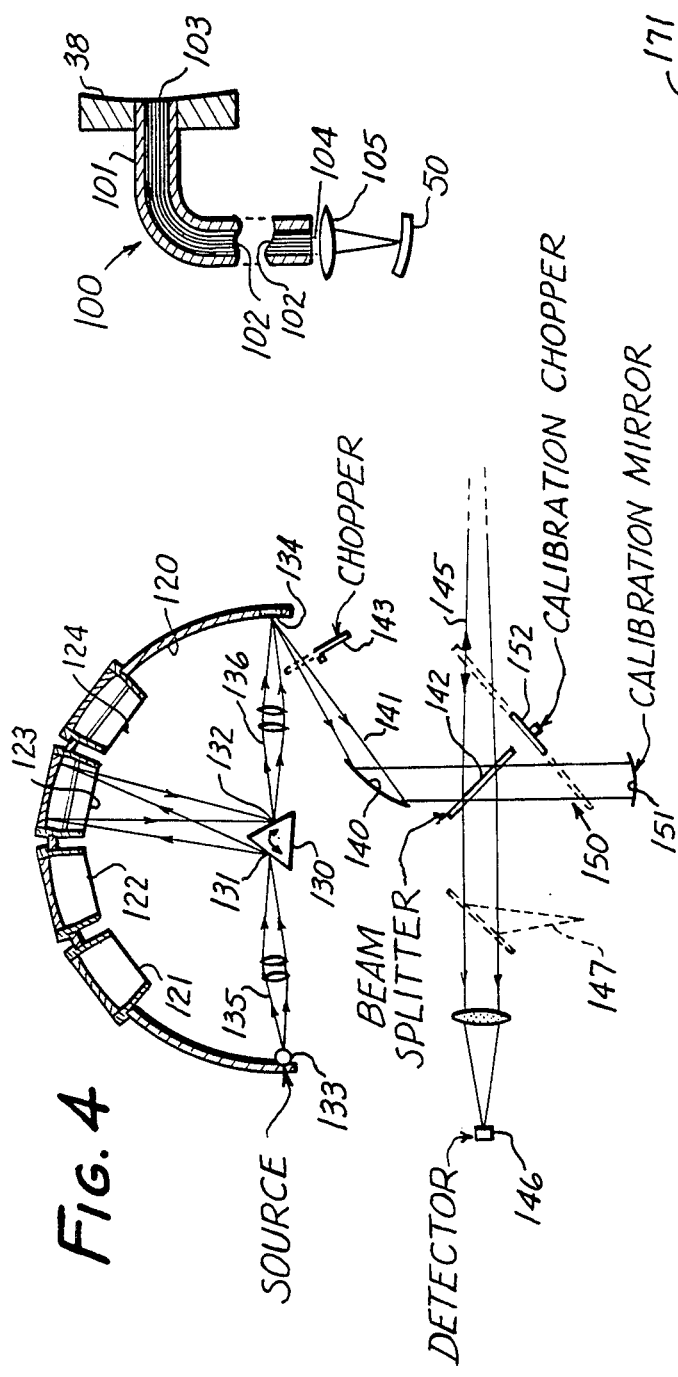

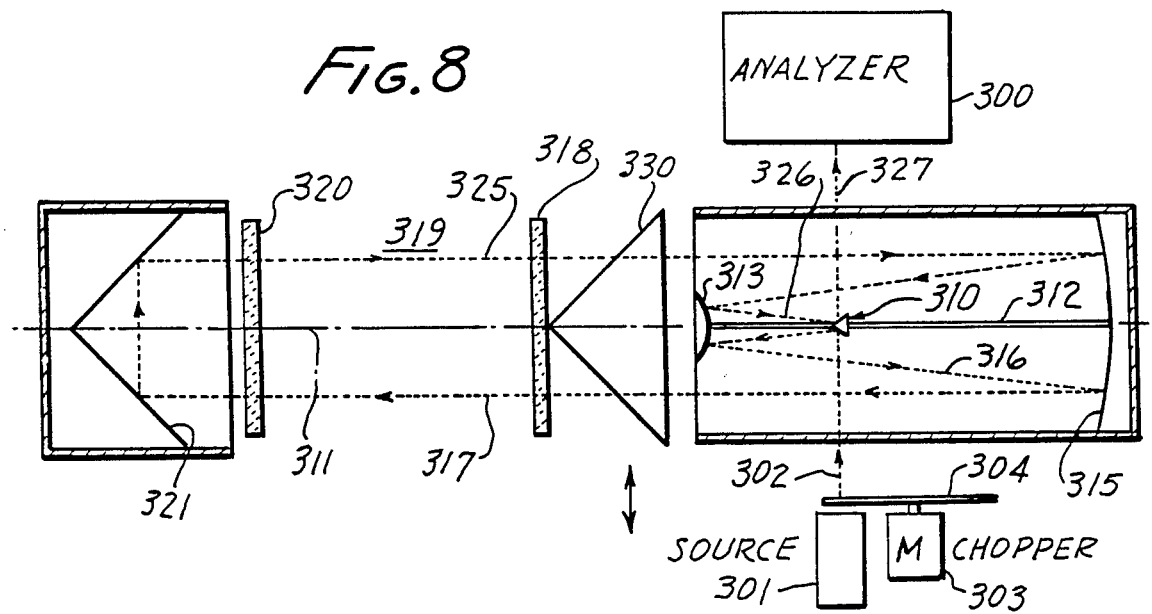
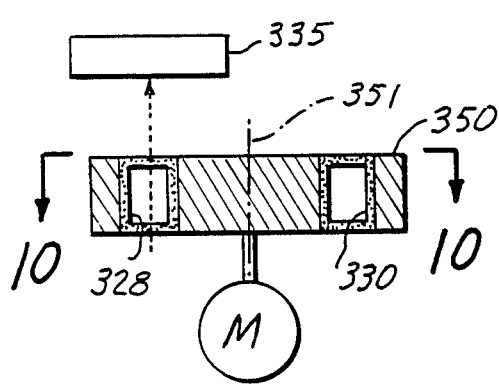
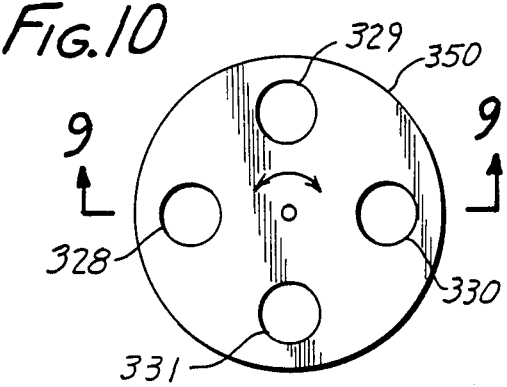
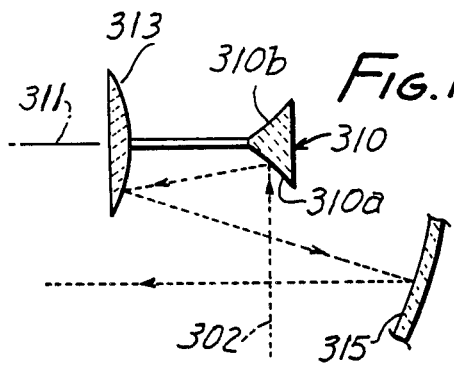
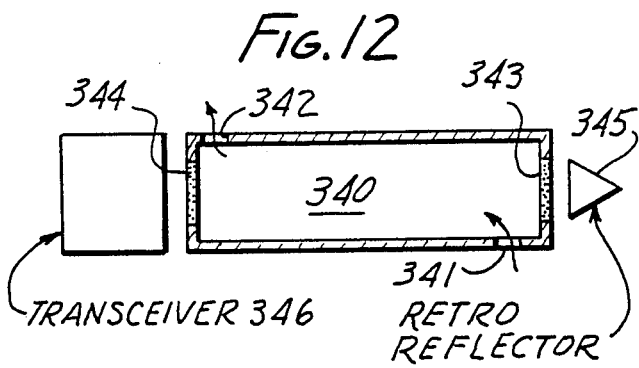

IN-SITU GAS ANALYZER

CROSS REFERENCE TO OTHER PARENT APPLICATION

This is a continuation-in-part of applicant's copending U.S. patent application, Ser. No. 470,146, filed Feb. 28, 1983, entitled "In-Situ Gas Analyzer", now abandoned.

FIELD OF THE INVENTION

This invention relates to instrumentation to measure concentration of a component gas in a gas stream, for example, the concentration of carbon monoxide in the exhaust gas stream from a gas-fired, coal-fired, or oil-fired boiler.

BACKGROUND OF THE INVENTION

Operators of combustion devices such as boilers have become increasingly aware that continuous detection and measurement of gases produced in minor quantities such as carbon monoxide, and responsive control of the processes which produce them, can result in dramatically improved fuel efficiency. For example, the provision of excess air was formerly widely used in combustion processes on the assumption that a lean mixture would assure more complete combustion of the fuel. However, as combustion processes became better understood, it also became apparent that the use of excess air was wasteful, because among other things it required the flame to heat excess gas, enabled the formation of $SO_3$ instead of merely $SO_2$, encouraged the formation of NO, created sulfate emmissions, and in some cases even increased smoke formation by shortening the flame length. Combustion operations using low excess air improve all of the above situations, but the control must be accurate, and be quickly responsive in order to insure complete combustion while avoiding uneconomical operations and the formation of excessive pollutants. The concentration of carbon monoxide produced by a combustion process turns out to be a good measure of the average combustion quality, i.e., nearness to stoichiometric condition. No CO means too much air, while high CO means not enough air.

With the realization that controls based on the concentration of some minor component of a gas stream can lead to an optimized combustion function, serious development of suitable instrumentation was undertaken, especially instrumentation for measuring the concentration of carbon monoxide in a gas stream. Of course, measuring techniques and instruments had long existed for this purpose, but frequently they relied on sampling techniques which were too slow to provide useful data for on-line adjustment of combustion parameters, or not reliable enough for continuous duty.

The increased stringency of government regulations relating to power plant emissions has long been a prod for the development of in-situ gas analyzers, and several types of such analyzers have been installed in hundreds of power plants in recent years. Some utilize the technique known as "gas filter correlation", which is a technique utilized in the instant invention. It is an object of this invention to employ this technique to better advantage in a gas analyzer whose sampling is done "in-situ", meaning without removal of a sample from the stream, but instead securing data as the consequence of measurements or observations of spectral energy which has been subjected to interaction with the gas stream itself—either by having passed through the gas stream or by having emanated from it.

Gas filter correlation is a well-known procedure which does not require description here for an understanding of the invention. A useful reference on this subject is "Analytical Methods Applied to Air Pollution Measurements" by Stevens and Herget, Chapter 10, pages 193-231, published by Ann Arbor Science, 1974, which is incorporated by reference herein for its showing of the applicable theory.

It is an object of this invention to provide a gas analyzer which can have a direct zero and span measurement, even with process sample gas continuing to flow through the process; which can readily and automatically be calibrated, and all interferences automatically rejected; which can be constructed so as readily to be accessed for routine repair and maintenance, and even disposed at a considerable distance from the stack; which is sufficiently heat resistant that its readings do not stray during temperature excursions; which rejects spurious signals from its surroundings; and which is forgiving of substantial physical shifts and changes in the physical environment, such as by expansion and contraction.

Still further objects are to provide better techniques for internal calibration of the instrument, for more efficient optical path, and for decreased sensitivity to external physical distortions such as vibratory and temperature induced dimensional shifts, as well as to interferences from changing gas stream chemical composition.

BRIEF DESCRIPTION OF THE INVENTION

A gas analyzer according to this invention utilizes spectral energy which has been subjected to interaction with a gas stream, either by having passed through the stream, or by having emanated from it.

The heart of this invention is an analyzer with an array of gas cells for reference and optionally for calibration, to which a beam of spectral energy is directed. The beam will, before or after interaction with these cells, also interact with the gas stream, either by being passed through the gas stream, or by having emanated from it. A detector is responsive to the energy which has interacted both with the gas stream and with the reference cells (optionally also with the calibration cells).

In one embodiment, the analyzer supports the cells relative to a movable deflector device which is movably related to two fixed beam segments. When this small device moves, it directs one of the beams to a selected one of the cells, receives the reflected beam from the cell and directs it along the other fixed beam segment. Thus, the analyzer operates within itself to direct the energy to be analyzed to selected cells, but can be placed anywhere that it receives an incoming beam segment, which can be fixed, or where it can produce a beam to be passed to the stack, which beam can also be fixed. Optional means can be provided to present different cells to the beam from time to time.

Optical devices can be placed in the path of the beam at appropriate locations to exert a focusing action which assures that regardless of physical shifts or movements of reasonable magnitude, the beam will fully fall onto the face of the detector. In other portions of the system, cassegrainean optics and/or cube corner reflectors can be provided which also reduce sensitivity to dimensional variations.

In one embodiment, a spectral source provides a beam which is passed twice through the gas stream (being reflected after the first pass). Alternatively, the source for one of the fixed beams may be emissions from the process or from the gases themselves.

In another embodiment, the spectral beam may be passed a single time through the stack gases, and then received and treated by the analyzer. This embodiment may also be adapted to receive and treat a beam of energy derived directly from the gas stream itself, by emission, or by "observing" the process itself, such as by receiving energy from a process flame in a burner, or from the gaseous region above a process, such as just above the molten glass surface in a glass furnace.

The reference cells can contain mixed gases to measure parameters of more than one gas, whose pertinent spectra do not interfere with one another. Carbon monoxide and sulfur dioxide constitute one such mixture.

According to yet another preferred but optional feature of the invention, a chopper is placed in the energy path between the source and the sample, whereby to provide pulses of energy to the detector at a frequency determined by the chopper, thereby providing means to reject spurious data.

According to yet another preferred but optional feature of this invention, a separate calibration beam path is provided which by-passes the stream on its way to the analyzer in order to give a zero-based reading.

According to still another preferred but optional feature of the invention, a pair of cube-corner retro-reflectors are provided to return the beam, one on each side of the gas stream, one to return the beam across the stream, and the other to return it in a calibration mode without crossing the gas stream.

According to yet another preferred but optional feature of the invention, the cells used for calibration have two separate gas chambers containing gases at different concentrations and pressures in order to provide two sets of data for the solution of two simultaneous equations.

The above and other features of this invention will be fully understood from the following detailed description and the accompanying drawings, in which:

BRIEF DESCRIPTION OF THE DRAWINGS

FIG. 4 is a top view of another embodiment of the invention;

FIG. 6 is a fragmentary view of still another embodiment of the invention;

FIG. 7 is a fragmentary schematic view showing means for placing the instrumentation at a greater distance from the gas stream;

FIG. 8 is a partially-schematic axial view of the presently preferred embodiment of the invention;

FIG. 9 shows an alternate means to present various cells;

FIG. 10 is a cross-section taken at line 10—10 in FIG. 9;

FIG. 11 is a fragmentary enlargement of part of FIG. 8; and

FIG. 12 shows an alternate sampling technique.

DETAILED DESCRIPTION OF THE INVENTION

Figure 1:
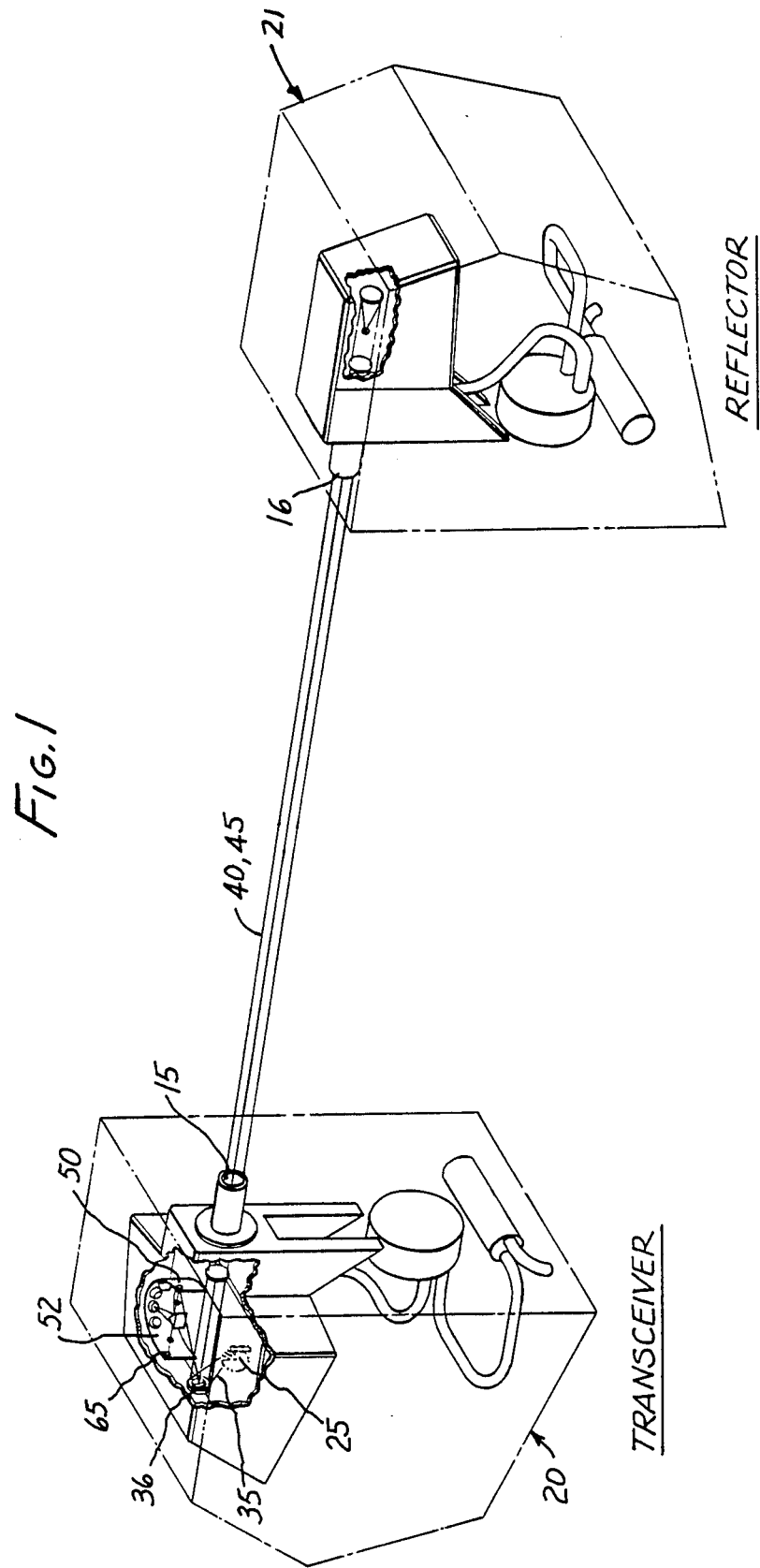
FIG. 1 is a perspective view of one embodiment of the invention.
Figure 2:
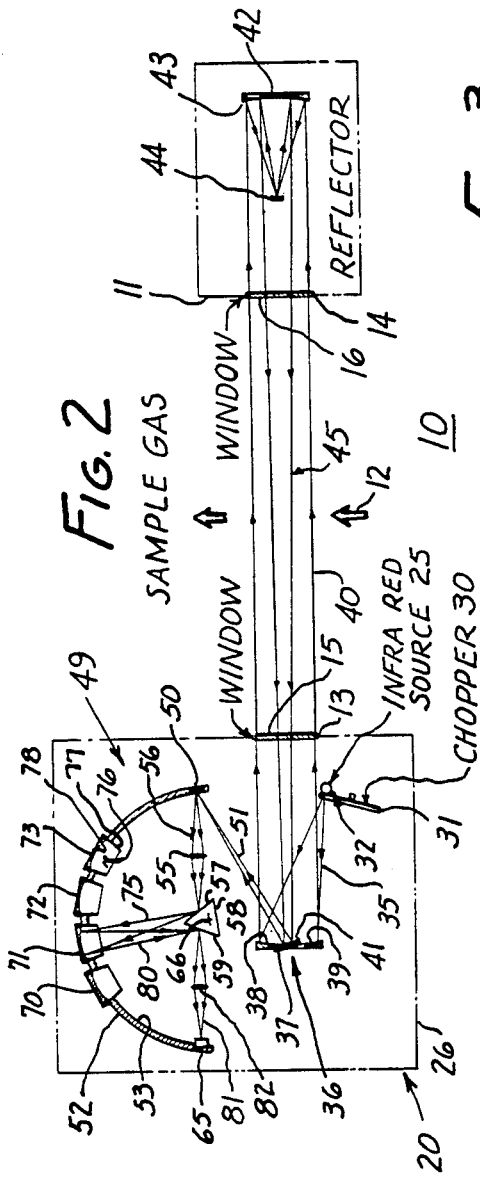
FIG. 2 is a top view of FIG. 1.

FIGS. 1 and 2 show an illustrative and useful embodiment of this invention, installed so as to measure the concentration of a selected gas in a gas stream. This example is a double-pass instrument, the beam passing twice through the gas being sampled. In the example given, the gas being observed is carbon monoxide. However, any other gas or substance subject spectrographic analysis could instead be detected and measured by appropriate modification of the instrument. Therefore, the scope of this invention is not to be limited to carbon monoxide analysis.

A gas stream containing carbon monoxide (or other gas whose concentration is to be measured) passes through a conduit such as a duct or a stack 10 (shown schematically) from a combustion device such as a boiler (not shown), on its way to atmosphere. Such a conduit will have a continuous peripheral wall 11 through which gas stream 12 flows.

This invention is not limited to use with gas streams in stacks or ducts. Such an example is given to show the best mode contemplated for its use at the present time. It is also applicable to observation of gases at the situs of the process, such as by analyzing spectra from the process itself. An example is a flame, directly observed. Another example is the observation of the gaseous region above a process, for example, above the glass surface in a glass furnace.

Two ports 13, 14 are formed through the wall of the duct, and respective windows 15, 16 are placed in them to provide observation access for the instrument. The window glass should not be absorptive of wavelengths of interest. For carbon monoxide analysis, sapphire glass is suitable.

The windows are accessible so they can be cleaned. Because they are frequently located at inconvenient locations, means can be provided to increase the length of time between cleanings. One such means is a nozzle manifold placed adjacent to, and just upstream from, the window. Air blown out of these nozzles forms a region of increased pressure along the surface of the window, thereby isolating the window from materials in the stream which might adhere to the window and reduce the transmission. Ultimately the windows will become excessively soiled and will have to be cleaned, but much less frequently than if this feature is not provided.

A transceiver module 20 is mounted to the conduit wall adjacent to one of the windows. A reflector module 21 is mounted to the stack wall adjacent to the other window. In fact, if preferred, the windows can be formed as part of the modules, and can be reached for cleaning by backing the modules away from the stack wall.

An emitter 25, of spectral energy, in this case a source of infrared energy in the band range between about 0.5u and 10u, is mounted to housing 26. The presently preferred emitter is a cartridge heater, but one alternate source might be a conventional home appliance igniter. Such igniters are inexpensive and durable. Despite the fact that they were designed for intermittent usage, they perform very satisfactorily over a long term of continuous use, glowing a dull red color, and emitting infrared energy in the said band which is useful for infrared spectroscopy.

To provide a pulsed beam, a rotating chopper wheel 30 is rotatably mounted in a path of the energy from the source. The wheel is driven by a motor (not shown) at a rotational velocity which will produce pulses of the correct frequency. The wheel has an opaque structure 31, with transmissive portions 32 through the structure. These portions may conveniently be open slots, open at the edge of the structure. Their number and width is selected so that, with a selected rotational velocity, energy pulses of the correct duration and frequency pass through the wheel.

A divergent beam 35 of infrared energy leaves the chopper wheel, and impinges on a two component mirror 36. In its most convenient configuration, the mirror is generally circular, although it need not be that shape. If it is, it can be made quite compact, with a first central component 37 and a ring-like second component 38 surrounding the first component.

Component 38 is a collimating reflector. It collects energy which impinges on its front surface 39 and directs the energy in a collimated beam segment 40. Component 37 has a reflecting front surface 41, and its central axis is tipped to the extent that energy which impinges on it that has passed the chopper wheel but was not included in the collimated beam impinges on baffles or other means which exclude it from the detection or analysis parts of the system.

Beam segment 40 (which is "tubularly" sectioned) passes through the two windows and the gas stream on the first pass through the sample gas. It impinges on a reflector mirror 42 which has an outer annular portion with a reflective first surface that acts in a Cassegraine manner. This is to say that it first reflects the beam to a focal mirror 44. The focal mirror then reflects the beam back to a center portion of reflector mirror 42, which then reflects the energy toward the transceiver module as a collimated or even a convergent beam 45.

Beam 45 passes through the two windows and the gas stream, and constitutes a second pass through the sample gas. A portion of beam 45 impinges on component 40 of the two-component mirror. The axis of component 37 is so disposed and arranged as to direct the beam to an initial mirror 50 (sometimes called an "initial reflector") of the housing of an analyzer 49. The curvature of component 37 is such that beam 51 from component 37 is focused on the initial mirror. For convenience, the housing may include a mount 52 with a wall 53 shaped as part of an axially-extending cylinder to support and align the initial mirror and other elements yet to be described. Initial mirror 50 is fixed to wall 53. Its reflected beam segment 56 will therefore also be fixed.

A focusing lens 55, or set of lenses, is disposed in the path of beam segment 56, to focus the energy toward a reflecting surface 57 carried by a rotatably mounted deflector 58. A second reflecting surface 59 is also carried by deflector 58. Surfaces 57 and 59 are planar, and form a dihedral angle between them for a purpose yet to be explained. A bi-directional motor 60 rotatably drives deflector 58 in an oscillatory movement between selected angular positions. The angle between surfaces 57 and 59 is such that beam segment 81 from surface 59 is fixed. Beam segments 56 and 81 are sometimes referred to as "first" and "second" fixed beam or fixed beams segments.

A detector 65 is mounted to wall 53, aligned with beam segment 81. The center of rotation 66 of deflector 58 lies within the dihedral angle of surfaces 57 and 59.

A plurality of gas cells 70, 71, 72 and 73, whose function and detailed construction will be described later are fixed to wall 53 in the same plane as the detector and the initial mirror. The axis of rotation of deflector 58 is normal to this plane.

Accordingly, the beam from the initial mirror impinges on first reflecting surface 57, which reflects the beam as beam segment 75 to a selected one of the cells. The selection of cells is accomplished by rotating deflector 58 to an angular position such that beam segment 75 impinges on the intended cell. Each cell has a gas-containing envelope 76, a transparent window 77, and a mirror 78 facing toward the deflector. They have gases in them which may be the same gas or a different gas, or a mixture of gases at the same pressure or concentration or at a different pressure or concentration, depending on the intended purpose. Some of them have more than one gas compartment, as will later be discussed. The alignment and curvature of mirrors 78 is such that the beam is reflected as segment 81, which includes a focusing lens 82.

It will be observed that segments 56 and 81 are fixed and do not move. They are not necessarily directly aligned as shown, and often will not be. Focusing by mirror 37 and by lenses 55 and 82 enables the analyzer to function accurately even if there is some shift or dislocation in the system outside of the analyzer. Such a dislocation might be caused, for example, by uneven heating of the stack, which would cause some misalignment in the system. The beam must simply reach the detector, and be brought to a focused (not necessarily a sharp focus) size which is smaller than the area of the detector. Thus, the focused beam spot on the detector might move around the surface of the detector, but will always be within its active area. In calling beam segments 56 and 81 "fixed" it is intended to say that even though there may be some movement within the segment itself, it is not manipulated in the selection of the cells. Such manipulation is done only on the segments between the deflector and the cells. Deflector 58 with its first and second reflecting surfaces 57 and 59, directs the beam to a selected cell, the selection depending on the angular position of the deflector, so that selected ones of the cells can be included in the sampling beam that extends from the source to the detector. Thus, this analyzer is adapted to use gas filter correlation spectroscopy. In this technology an energy beam is passed through a correlation gas cell (at a separate time), instead of through a reference gas cell when it passes to the detector, and at another time through a reference gas cell. Thus, one of cells 70-73, say cell 70, is a correlation cell, and another cell, say cell 71 is a reference cell. Cells 72 and 73 are calibration cells. Their construction and function will be discussed below.

In the typical gas filter correlation instrument, a leak in the correlation cell results in a change in absorption at the line centers, causing a change in the instrument drift. As described below, this instrument uses multiple gas cells with fixed and known relationship one to another. The electronics automatically check this relationship and compensate, and can be instrumented to alarm if one cell has changed relative to the others.

Across-the-stack instruments, with or without a cross-stack pipe or other rigid support, have demonstrated sensitivity to alignment changes. As the sun shines on one side of the stack, or when process parameters change, temperature changes in the stack or duct wall cause differential movement of one side relative to the other. The optical components of the instant system (mirrors and lenses, especially the lenses in the analyzer) can correct for these variations, when they are designed with these variations in mind.

Figure 3:
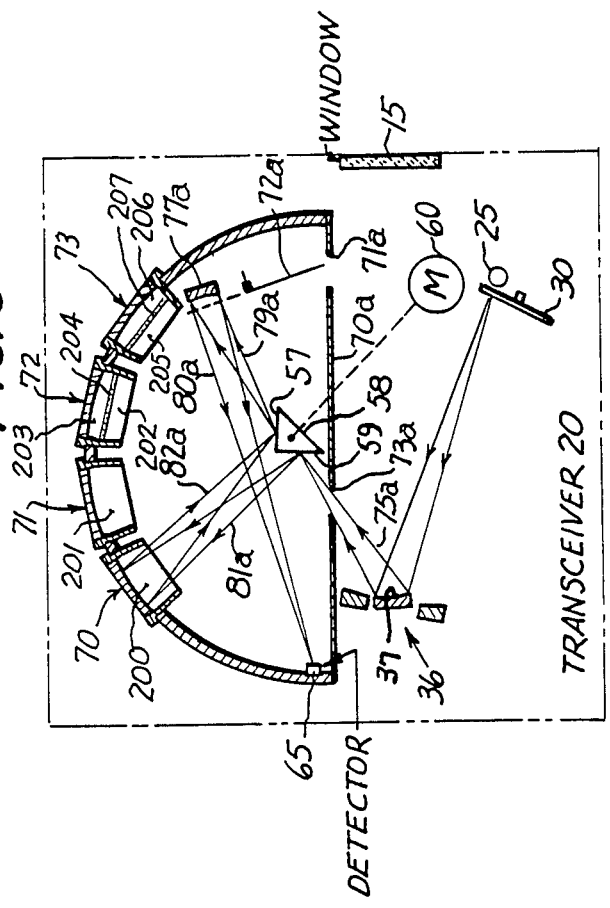
FIG. 3 is a fragmentary view of FIG. 1, operating in a calibration mode.

When the embodiment shown in FIGS. 1 and 2 is used, calibration of the instrument is conducted with the use of an infrared beam from the source which beam is not passed through the gases to be sampled or measured. Instead the beam is sent directly to the analyzer, as best shown in FIG. 3. FIG. 3 is a showing of the same system as that shown in FIG. 1, but illustrates a baffle system. Identical parts bear identical numbers.

In FIG. 3, baffle 70a is shown with a first aperture 71a that passes the beam returned from the stack. A shutter 72a intersects beam 51 when calibration is done. At that time shutter 72a is in the solid-line position shown. When measurement is to be done, the shutter is rotated to the dotted-line position, which interesects a calibration beam 75a now to be described. The calibration beam passes through a second aperture 73a in the baffle.

Calibration beam 75a is reflected from the source by mirror central component 37, and converges toward reflecting surface 59 on deflector 58. This beam strikes the "back" surface of the deflector. Beam 75a is reflected to the individual ones of the cells as appropriate and is reflected back to surface 57 on the mount, which in turn reflects it to a concave calibration mirror 77a that focuses the beam on the detector. It will be observed that beam segments 75a, 79a, and 80a are fixed, but that segments 81a and 82a move from cell to cell when mount 58 is rotated.

The basic instrument signal processing electronics are remotely located from the instrument box so as to increase their accessibility and to allow them to be placed in a temperature controlled enviroment. The instrument box itself has the minimum amount of electronics required to operate the optical head. The detector preamplifier is mounted directly at the back of the detector. The power supplies and the stepper motor control, and other functions, can be located on a single printed circuit board below the optical base plate. The output of the optical head can be transmitted either by analog or digital means to a remote panel.

A microprocessor is used for signal processing at the remote panel. This includes setting the optical path length across the stack, full scale of the instrument, linearization of the output, automatic calibration, temperature compensation of the data, (through the input of a thermocouple readout in the gas stream), pressure compensation, adjustable high and low limit alarms, and diagnostics including power failure, blower failure, source failure, detector failure, stepper motor failure, leak in a gas cell, dirty windows, high temperature alarm for the detector, high temperature alarm for the instrument box, and electronics failure, as examples.

Both the instrument box and the reflector box and the associated air purge blowers and filters, as well as the junction box for power in and signals out can all be enclosed in a weather-tight box for basic instrument weather protection.

Yet another way to remove the more sensitive elements of the device to a more favorable environment is shown in FIG. 7. The instrument is responsive to infrared beams that have passed through or emanated from the gas stream. While it is good practice to place the instrument near to the substances it measures or reacts to, sometimes this is inconvenient. Electronic transmission of the raw data also involves problems.

This invention provides the advantage that the optical system can be interrupted at various places, and coupled by optical forwarding means of various types. The presently-preferred such optical forwarding means is a fiber optic bundle. This is shown in FIG. 7, where a typical fiber-optic bundle 100 having a sheath 101 and a large number of glass fibers 102 has one of its ends 103 fitted in the aperture in ring-like component 38, in place of central component 37. Its bundle receives energy from beam 45. The fibers conduct this energy to end 104, and a focusing lens 105 focuses it onto initial mirror 50, wherever it is placed. The bundle can be bent and can be of any length so the result is to enable the deflector and cells to be placed more conveniently for the user. The glass fibers will be coated with an external reflecting coating in accordance with known fiber-optics techniques.

Other optical forwarding means can be used instead. An example is the classical rod-lens telescope shown in Hopkins U.S. Pat. No. 3,257,902. However, this device does not readily accomodate bends, and may be more difficult to employ. It does have image-forming properties superior to those of fiber glass bundles, even of coherent fiber bundles, should image properties be of interest.

The embodiment of FIGS. 1 and 2 is characterized as a double pass system. In a double pass system, the beam is twice subjected to the effects of the gas stream, having been directed through it, and then reflected back through it again. In this embodiment, the source is separate from the cell mount, and the detector is held by the cell mount.

There are circumstances in a double pass system where it is preferable for the source to be mounted to the cell mount, and for the detector to be located elsewhere: FIG. 4 shows one such arrangement. In the embodiment of FIGS. 1 and 2, the beam is passed through the cells after having been passed twice through the gas stream.

In FIG. 4, the beam is passed through the cells before it is passed through the gas stream. As it happens, it is also passed twice through the gas stream. The net result in absorption spectroscopy is the same in both FIGS. 1 and 4. A wall 120 identical to wall 53 supports four cells, 121, 122, 123, and 124, which are identical to cells 70, 71, 72, and 73, respectively. A rotatable deflector 130 having reflective surfaces 131, 132 is identical to deflector 58. An infrared source 133 is mounted to wall 120 where detector 65 is in FIG. 2, and a mirror 134 (for convenience sometimes called an "initial mirror "or" initial reflector", as used for mirror 50, even though it is not the first mirror to be impinged on by the beam) is mounted to wall 120, where mirror 50 is located in FIG. 2. Thus, except that an infrared source has been substituted for the detector, this part of FIG. 4 is identical to the respective part in FIG. 2.

Fixed beam segments 135 and 136 are on opposite sides of the deflector, with respective lenses 137 and 138. Reflecting surfaces 131 and 132 reflect incident energy as shown. The back walls of the cells are mirrored as before.

A concave mirror 140 reflects beam 141 from mirror 134 to a beam splitter 142. The beam splitter is a partially reflecting mirror which transmits about half and reflects about half of the energy incident upon it. A chopper 143 identical in form and function to chopper 30 is interposed in beam 141.

Beam 145 to the right of the beam splitter corresponds to the beam reflected by mirror 39 and reflected by the reflector in FIG. 2. The portion to the right is identical to that in FIG. 2, and is not repeated in the drawings.

A detector 146 similar in form and function to detector 65 in FIG. 2 receives the treated beams.

An optional semi-reflecting mirror 147 is shown which might be such as a hot or cold mirror to deflect energy of different wavelengths to be measured for some purpose.

For purposes of calibration, a calibration segment 150 extends below beam splitter 142 to a reflecting mirror 151 that reflects the beam back to the beam splitter. The portion which is reflected to the left is received by the detector. The part which passes through is ignored. A calibration chopper 152 blocks beam 145 for the calibration cycle, and then blocks beam 150 for sample measuring.

Figure 5:
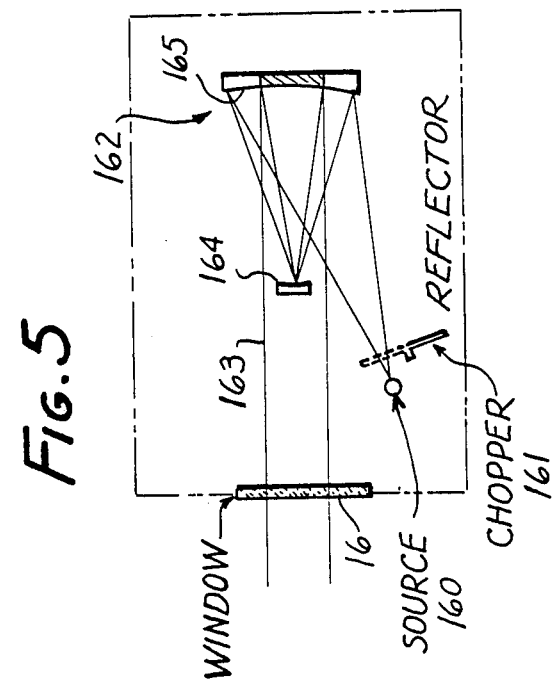
FIG. 5 is a fragmentary view of yet another embodiment of the invention.

Thus, FIG. 4 is a double pass instrument with the source and detector in effect interchanged in position. FIGS. 5 and 6 are single pass instruments. In FIG. 5, a beam is projected through the gas stream. In FIG. 6 the energy to form the beam emanates from the gas stream itself.

FIG. 5 functions together with all of the equipment shown to the left of the gas stream. Instead of merely returning a beam across the gas stream, it originates the beam, utilizing an infrared source 160, chopper 161, and a reflector system such as the Cassegraine-type 162 that projects a beam 163 across gas stream, where it passes through window 15 and is treated by the remainder of the system in FIG. 2. Of course, chopper 30 is not used at this time. Instead of the Cassegraine system, mirror 165 may collimate the beam directly.

When calibration is to be done, the separate system of FIG. 3 will be used, the relationship between the two sources being known.

FIG. 6 utilizes emission spectroscopy instead of absorption spectroscopy in the equivalent of a single pass system. A window 170 in the wall of a duct 171 for a gas stream 172 that emanates infrared energy passes energy to collimating lens 173 that forms a beam 174 which impinges on a focusing mirror 175. This beam is reflected to initial mirror 50, and is treated by the remainder of the system of FIG. 2. A chopper (not shown) can be placed in the path of the beam. For calibration, the separate calibration system shown in FIG. 3 can be provided. In all embodiments, when changing from a calibration to an active measuring mode, appropriate shutters will be moved to exclude confusing or extraneous beams from the system. Some of these are not shown, because their purpose and possible locations are evident.

Cells useful in the analyzer and in the system, and their use, will now be described. Cell 70 is referred to as a "correlation" cell. Cell 71 is referred to as a "reference" cell. Cells 72 and 73 are referred to as first and second "calibration" cells, respectively.

Cell 70 has a single gas-tight compartment 200. It contains gas of the type being measured, for example carbon monoxide at a partial pressure of generally the same partial pressure as the substance exists in the sample being measured, and another gas as a broadening agent, for example, nitrogen. The other gas increases the total pressure in the compartment 200 to a pressure that is subatmospheric, and such that the line widths in the spectrum from this cell in use will be about the same as the line widths in the spectrum from the sample in the process being measured. In use, correlation cell 70 provides a measurement of background intensity.

Reference cell 71 has a single gas-tight compartment 201. It contains a quantity of the gas being measured at about the same partial pressure as in cell 70. It also contains broadening agent, the same as in cell 70, but this agent is supplied in an amount such that the total pressure is greater than in cell 70. This broadens the lines giving a similar total absorption, but a significantly lower absorption at the line centers.

First calibration cell 72 has two gas tight compartments 202, 203, which are serially located in the beam, with a transparent wall 204 between them. Compartment 202 contains a known partial pressure of the "sample" gas, i.e., a known partial pressure in a total pressure (in the presence of nitrogen gas, for example) at a subatmospheric pressure. Compartment 203 is equivalent to the reference cell, and contains "sample" gas at approximately the same partial pressure and total pressure as in cell 71.

Second calibration cell 73 has a first and second compartment 205, 206 respectively, as in cell 72. Compartment 205 contains the same gases as compartment 203, but with the sample gas at a known, higher partial pressure. Compartment 206 contains the same gases at the same pressures as compartment 204.

Broadly stated, the filling of correlation cell 70 is such that the absorption line widths in the correlation cell, which is at the ambient temperature of the instrument box, are essentially identical to the line widths in the gas stream containing the sample. Applications for this instrument will normally range from gas stream temperatures of about 250° up to about 750°. Applications outside of this temperature range are also possible. Sufficient absorbing gas partial pressure is utilized in the correlation cell to insure essentially complete absorption of the line centers at those wavelengths where the sample gas absorbs. With a narrow band pass filter in front of the detector which transmits energy only in wavelength band ($\Delta\lambda$) where the sample absorbs, then the only energy seen by the detector when the correlation cell is in the beam is that energy which is transmitted through the gas stream at those interleaving wavelengths where the sample does not absorb.

The reference cell will be filled to a higher total pressure such as 5 atmospheres. This causes absorption at the same wavelengths, but because of the higher total pressure the absorbing lines are much broader. The detector then alternately sees a beam which passed through the correlation cell with complete absorption of sample, giving only the background radiation, and then the beam which has passed through the reference cell, giving the background radiation plus a partial absorption of CO (caused by the CO in the stream and in the cell). Since the background is the same through both cells, the change in absorption by the sample in the reference cell is directly proportional to the concentration of the sample in the gas stream.

The calibration cells provide an up-scale instrument calibration point. With the zero and span information, a microprocessor based set of electronics (which is located remotely from the analyzer) can provide a periodic automatic full calibration and output adjust in accordance with known procedures.

The two calibration cells differ from the correlation and reference cells in that each one has two compartments. One compartment contains the low concentration calibration/span gas, and the other compartment contains the equivalent of the reference cell, but at known concentrations. Therefore, although the beam does not pass through the sample, this effect is reproduced on a known concentration. Thus, the beam passes through the reference cell and a known span concentration, and then to the detector. The signal seen at the detector is compared to that seen after the beam has passed through the correlation cell for direct calibration.

As part of a calibration cycle, the sample beam is sequentially stepped through each of the two calibration cells. This provides two incrementally added known concentrations to the unknown stack concentration. These two additional data points allow the computation and elimination of zero and span offsets, such as the measurement of CO. These are $H_2O$ and $CO_2$. This recalibration cycle is done frequently, at a selected frequency, which may be adjustable. Five minute intervals are generally satisfactory.

FIG. 8 shows the presently preferred embodiment of the invention. It enables the available radiant energy more efficiently to be used, and the instrument to be less sensitive to external distortive forces, in addition to other advantages.

The objective of the system is, as before, to provide to an analyzer 300, a beam which has passed or will pass through a gas sample, or cells. This can be, and most frequently will be, the same as analyzer 50. The analyzer of FIG. 4 is also useful. There are other viable analyzers, as will later be shown.

An infrared source 301 emits infrared energy along path segment 302. A chopper 303, which conveniently comprises a bidirectionally rotatable notched disc 304 is in said path. The spacing of the notches and the speed of rotation of the disc determines the chopping frequency. 900 Hz is a useful frequency when this device is used to screen out background noise and interference.

A two element deflector mirror 310 is disposed on the central axis 311 of the optical system. A baffle 312 extends axially along the system to divide it into two halves. It occludes path segment 302, and divides into two elements the mirror 310, and a focal mirror 313.

Mirror 310 has a first reflective element 310a which reflects rays along segment 302 to focal mirror 313. Element 310a will be generally concave, and will direct the rays to domed focal mirror 313. Domed mirror 313 will direct the impinging rays onto Cassegrainean mirror 315 along path 316 which in turn will reflect them along a collimated path 317, which is half-tubular, axially.

Path 317 exits through window 318, crosses stack 319, passes through window 320, and impinges on a trihedral retroreflector 321. This is a classical cube-corner reflector comprised of three mutually perpendicular mirrors. The beam represented by path 317 is therefore rotated 180°, and displaced to the other side of the plane defined by baffle 312. The rays are returned precisely parallel, along path 325 and impinges on the other half of the Cassegrainean mirror, which in turn reflects them to the other part of the focal mirror, which in turn reflects them along path 326 to the other side of deflector mirror 310. The shape of element 310b is such as to direct the rays in a path 327 to analyzer 300. Rays in path 327 can be treated precisely as in FIGS. 1–7.

As before it is necessary to have an optical path which does not include the sample in order to provide for calibration. In this embodiment, this objective is readily met by providing a second retroreflector 330 between the Cassegrainean mirror and the stack. This retroreflector is identical to retroreflector 321. It may be placed in the way of path 317, and will return the rays on that portion of path 325 which does not include the sample. The second retroreflector can be mounted on a slide to be removed when not desired. This is an elegant means to provide two effective paths, with all of the advantages available to both.

FIGS. 9 and 10 illustrate that many of the advantages of this invention can be attained with a different means to mount the cells, and without using a rotatable deflector. In FIG. 9, a wheel 350 is shown bi-directionally rotatable around an axis 351 which is parallel to and offset from path 327. This wheel has a plurality of ports 328, 329, 330 and 331, each adapted to hold a respective cell, like cells 70–73, respectively. A detector 335 receives energy passed by the cells, and it corresponds precisely to detector 65 in FIG. 2. It is evident that the positions of the source and the deflector can be reversed.

In the embodiments already described, the gases in the stack are traversed by the beam, or are used as a source. It is equally within the scope of this invention to divert gas through a sampling chamber, and to use the gases in the sampling chamber the same as the gases in the stack. FIG. 12 shows a sampling chamber 340 with an inlet 341 and an outlet 342. Stack gases are diverted through the chamber, which is equipped with windows 343, 344. A reflector 345 is at one side, and the transceiver 346 (the analyzer and source) is at the other. All features of any of the embodiments are useful with the sampling chamber, or with the stack.

In this specification, the term "analyzer" is used for that portion of the system in which the beam is distributed to the cells, or the cells placed in the path of a fixed beam. That part of the system in which the calibration beam is formed, or the beam passed through the sample, is sometimes called "beam forwarding means."

The operation of the system as to absorption or emission, utilizing the principles and practices of gas filter correlation will be recognized by persons skilled in the art. This instrument and the applications it enables, is rugged and involves few moving parts. Importantly, it is forgiving for changes in alignments, and can be constructed if desired so as to require only the movement of beam segments, rather than cells, as a consequence of the simple stepping movement of a mirror-bearing deflector.

Spectral energy, i.e., wave type energy subject to absorption or emission interaction can be used, over the full range of spectral wavelengths, including ultraviolet, visible, and infrared. Of course, an appropriate emitter and responsive deflector must be provided. For most gas measurements, the infrared region is very suitable, and detectors responsive to wavelengths in this region are well-developed. However, the invention is not to be limited to usage in the infrared region, because absorption and emission phenomena in other bands or regions are also useful.

Systems according to this invention are elegantly simple and inherently rugged. The image-deflecting and forming elements are simple lenses and reflectors. Sharp images are not necessary, because it is only necessary that the beam be related to selected cells from time to time, and then arrive at the active surface of the detector. In some embodiments this instrument can be switched from calibration to measurement modes merely by shifting a shutter, and operates within its measurement mode merely by appropriate rotation of a mount which carries reflecting surfaces. In another embodiment the change of modes is made merely by shifting a retroreflector.

This invention is not to be limited by the embodiments shown in the drawings and described in the description, which are given by way of example and not of limitation, but only in accordance with the scope of the appended claims.

I claim:

1. In an instrument for measuring the concentration of a gas in a stream of other gases, utilizing a beam of spectral energy which has passed through or emanated from at least some part of said stream, an analyzer comprising:
   a plurality of gas cells spaced apart from one another;
   an initial reflector;
   a rotatable deflector, comprising a pair of deflecting reflectors rotatably carried by it, said deflecting reflectors forming an angle with one another, the center of rotation of said deflector lying inside said angle;
   means for rotating said deflector;
   a spectral source or a spectral detector, said cells, initial reflector, rotatable deflector and source or detector being fixedly located relative to one another such that fixed beam segments of said beam are formed between the initial reflector and the rotatable deflector, and between the rotatable deflector and the source or detector, and an angularly movable beam segment of said beam is formed between each of the deflecting reflectors of the rotatable deflector and the locus of said cells which movable beam segments can be moved from cell to cell as the consequence of rotation of the rotatable deflector, a first of said movable beam segments extending from one of said deflecting reflectors to said cell locus, and the other of said movable beam segments extending from the said locus to the other of said deflecting reflectors; and
   reflecting means adjacent to each said cell for reflecting the beam from one of said movable beam segments to the other, after the beam has passed through the cell at least once.

2. Apparatus according to claim 1 in which said fixed beam segments include focusing lenses.

3. Apparatus according to claim 1 in which said plurality of cells includes a correlation cell, a reference cell, and a calibration cell, said correlation and reference cells containing sample gas at approximately equal partial pressures, which, together with another gas provides a total pressure which is a sub-atmospheric pressure in the correlation cell, and higher total pressure in the reference cell, and, in the calibration cell two compartments in series, one of which contains sample gas with a partial pressure about proportional to the anticipated concentration in the gas stream, and a total gas pressure about equal to that in the correlation cell, and the other containing about the same partial pressure and total pressure as found in the reference cell.

4. Apparatus according to claim 3 in which a second said calibration cell is provided which constitutes a two compartment cell in which a different and known concentration of sample gas is contained at substantially the same total pressure as in the same first calibration cell.

5. In combination:
   apparatus according to claim 1; means for directing a beam through a gas stream, said means receiving said beam from said analyzer, or directing it to said initial reflector, and whichever of said source or detector is not carried by said analyzer, disposed on said beam spaced from said analyzer.

6. A combination according to claim 5 in which said detector, cells, initial reflector, reflecting means and rotatable deflector are fixedly mounted to common structure, and in which said beam is passed twice through said gas stream.

7. A combination according to claim 5 in which a separate calibration beam path is provided from said source to said deflector to provide a beam to or from said analyzer which does not pass through the gas stream.

8. A combination according to claim 5 in which said source comprises the gas stream itself.

9. A combination according to claim 5 in which chopper means is disposed in the path of said beam.

10. A combination according to claim 5 in which beam forwarding means is provided in the path of said beam to enable the analyzer to be located at an arbitrary location relative to said gas stream.

11. A combination according to claim 5 in which said fixed beam segments include focusing lenses, which maintain the image on said detector, even when the incident angle of the beam changes.

12. A combination according to claim 5 in which said means to rotate the deflector is a stepping motor.

13. A combination according to claim 7 in which said plurality of cells includes a correlation cell, a reference cell, and a calibration cell, said correlation and reference cells containing sample gas at approximately equal partial pressures, which, together with another gas provides a total pressure which is sub-atmospheric pressure in the correlation cell, and a higher total pressure in the reference cell, and, in the calibration cell two compartments in series, one of which contains sample gas with a partial pressure about proportional to the anticipated concentration in the gas stream, and a total gas pressure about equal to that in the correlation cell, and the other containing about the same partial pressure and a total gas pressure about equal to that in the reference cell, and a second said calibration cell comprising a a two compartment cell in which a different and known concentration of sample gas is contained at substantially the same total pressure as in the same first calibration cell.

14. In an instrument for measuring the concentration of a gas in a stream of other gases, utilizing spectral energy which has passed through or emanated from at least some part of said stream:
   an analyzer comprising a plurality of cells through which a beam of said energy is to be passed;
   beam forwarding means to direct an energy beam through or from said stream to said analyzer said beam being fixed as it enters said analyzer; and
   means in said analyzer to cause said beam to encounter selected ones of said cells;
   said beam forwarding means comprising a pair of axially spaced apart Cassegrainean reflecting systems.

15. In an instrument for measuring the concentration of a gas in a stream of other gases, utilizing spectral energy which has passed through or emanated from at least some part of said stream:
- an analyzer comprising a plurality of cells through which a beam of said energy is to be passed;
- beam forwarding means to direct an energy beam through or from said stream to said analyzer, said beam being fixed as it enters said analyzer; and
- means in said analyzer to cause said beam to encounter selector ones of said cells;
- said beam forwarding means comprising a two-element mirror, a focal mirror, and a Cassegrainean mirror so disposed and arranged that one element of said two element mirror and one half of said focal mirror and said Cassegrainean mirror form a substantially collimated beam occupying substantially an entire half-tubular path, a single retrodirective reflector in said half-tubular path which returns and rotates by 180 degrees the entire energy beam which it receives, and directs it to the other one half of the Cassegrainean mirror, which reflects it to the other half of the focal mirror and the other element of the two-element mirror, which in turn forwards the energy beam to the analyzer as said fixed beam.

16. Apparatus according to claim 15 in which said elements and Cassegrainean mirrors are concave, and the focal mirror is convex.

17. In an instrument for measuring the concentration of a gas in a stream of other gases, utilizing spectral energy which has passed through or emanated from at least some part of said stream:
- an analyzer comprising a plurality of cells through which a beam of said energy is to be passed;
- beam forwarding means to direct an energy beam through or form said stream to said analyzer, said beam being fixed as it enters said analyzer; and
- means in said analyzer to cause said beam to encounter selected ones of said cells;
- comprising a rotatable member carrying a pair of angularly related mirrors, one to direct a beam segment of said beam to a selected cell, and the other to receive a beam segment of the beam returned from the cell, and to direct it along a fixed path, the cells, reflecting means adjacent to the cells, and the rotatable member being fixedly mounted to common structure.

18. In an instrument for measuring the concentration of a gas in a stream of other gases, utilizing spectral energy which has passed through or emanated from at least some part of said stream:
- an analyzer comprising a plurality of cells through which a beam of said energy is to be passed;
- beam forwarding means to direct an energy beam through or from said stream to said analyzer, said beam being fixed as it enters said analyzer; and
- means in said analyzer to cause said beam to encounter selected ones of said cells;
- said plurality of cells including a correlation cell, a reference cell, and a calibration cell, said correlation and reference cells containing sample gas at approximately equal partial pressures, which together with another gas provides a total pressure in said correlation cell which is selected so that the line widths are approximately the same as the sample line widths, as increasing temperature and decreasing pressure narrows said lines, and a higher total pressure in the reference cell, and, in the calibration cell, a sample gas with a selected partial pressure about proportional to some fraction of the anticipated concentration in the gas stream, and total gas pressure about equal to that in the correlation cell.

19. Apparatus according to claim 18 in which said total pressures in said correlation and reference cells are subatmospheric.

20. Apparatus according to claim 18 in which a second of said correlation cells is provided with about the same partial pressure and total pressure as exists in the reference cell.

21. Apparatus according to claim 18 in which said beam forwarding means includes a single retroreflector to return and rotate an entire beam which has passed through the gas stream.

22. Apparatus according to claim 18 in which said beam forwarding means includes a single sample retroreflector to return and rotate an entire beam which has not passed through the gas stream, said sample retroreflector being mounted for selective insertion into and removal from the path of the beam.

23. Apparatus according to claim 22 in which another single reflector is placed in the beam so as to rotate and return an entire beam which has passed through the gas stream.

* * * * *